United States Patent [19]
Natterer

[11] Patent Number: 5,079,010
[45] Date of Patent: Jan. 7, 1992

[54] PHARMACEUTICAL PREPARATION FOR THE TREATMENT OF WOUNDS, DAMAGED TISSUE AND INFLAMMATION IN ANIMALS

[76] Inventor: Siegfreid Natterer, Galgenbergweg 1, 8475 Wernberg, Fed. Rep. of Germany

[21] Appl. No.: 410,984

[22] Filed: Sep. 22, 1989

[30] Foreign Application Priority Data

Sep. 22, 1988 [DE] Fed. Rep. of Germany ....... 3832211
Sep. 5, 1989 [DE] Fed. Rep. of Germany ....... 3929411

[51] Int. Cl.$^5$ .............. A61K 33/24; A61K 33/34; A61K 33/32; A61K 33/26
[52] U.S. Cl. ................... 424/617; 424/630; 424/639; 424/642; 424/643; 424/646; 424/648; 424/650
[58] Field of Search ............... 424/642, 630, 648, 646, 424/650, 617, 639, 643

[56] References Cited

U.S. PATENT DOCUMENTS

| | | | |
|---|---|---|---|
| 4,166,108 | 8/1979 | Brown et al. | 424/447 |
| 4,292,324 | 9/1981 | Jensson et al. | 514/494 |
| 4,330,527 | 5/1982 | Arima et al. | 424/94.5 |
| 4,581,227 | 4/1986 | Kjelleberg et al. | 424/49 |
| 4,582,907 | 4/1986 | Campbell | 548/194 |
| 4,680,309 | 7/1987 | Maurer | 514/499 |
| 4,847,083 | 7/1989 | Clark | 424/642 |

OTHER PUBLICATIONS

Benson, J. M. et al., Biochemical Responses of Rat & Mouse Lung to Inhaled Nickel Compounds, CA 111:128540d (1989).

Primary Examiner—Glennon H. Hollrah
Assistant Examiner—Gary E. Hollinden
Attorney, Agent, or Firm—Rosenman & Colin

[57] ABSTRACT

A pharmaceutical preparation for oral or transdermal treatment of wounds, damaged tissue and inflammation which is a solution containing water and metallic trace elements or salts thereof in a physiological quantity.

8 Claims, 1 Drawing Sheet

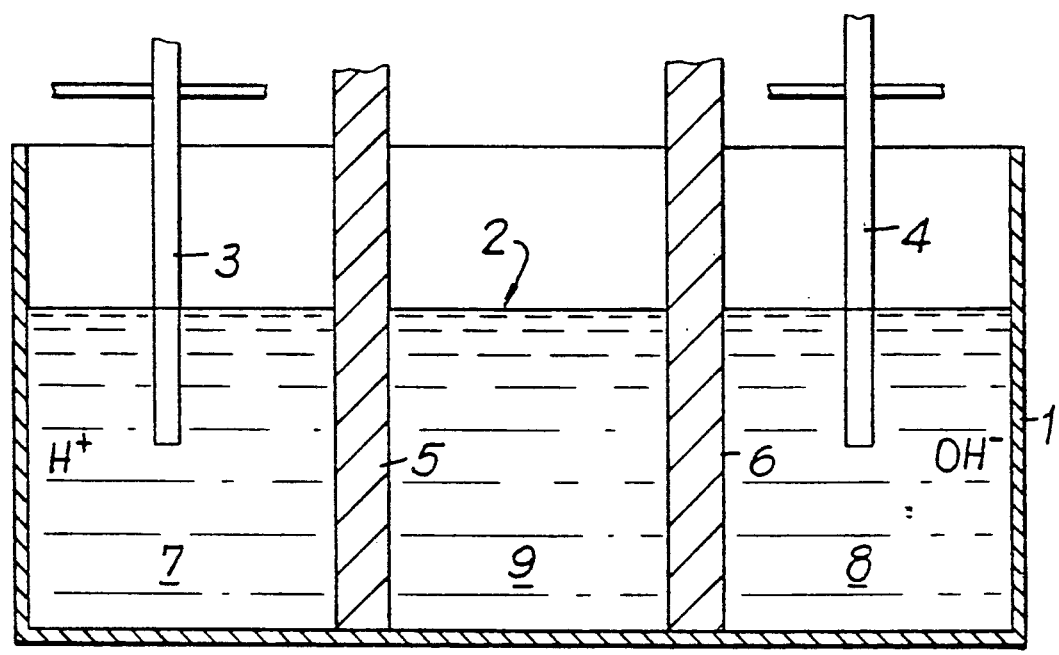

PHARMACEUTICAL PREPARATION FOR THE TREATMENT OF WOUNDS, DAMAGED TISSUE AND INFLAMMATION IN ANIMALS

The treatment of wounds with inorganic or mineral active substances is known in principle. Thus, for instance, zinc oxide is used to a large extent for both the prophylaxis and treatment of wounds, burns, etc., and therefore generally in the case of inflammatory changes of the skin and of the subcutaneous cell tissue, and also for poorly healing wounds and ulcers. Despite the widespread use of zinc oxide, the results obtained with it, however, are very frequently unsatisfactory.

The object of the present invention is to provide a pharmaceutical preparation and a method for the production of such a preparation which assure increased bio-availability, upon both transdermal and oral use.

In order to achieve this purpose, a pharmaceutical preparation corresponding to the body of claim 1 and a method of producing said preparation corresponding to the body of claim 8 are carried out. Preferred embodiments form the object of the subordinate claims.

The preparation of the invention, which is suitable for both oral administration (for instance in order to substitute for a lack of trace elements) and transdermal use assures, in each case, a high bio-availability of the metallic trace elements present, so that the desired therapeutic effect is obtained even in small doses.

The preparation of the invention, which is also characterized by good compatibility with the mucous membranes, has the following pharmacological properties, in particular upon transdermal use:
inflammation-inhibiting action
anti-coagulative action (especially fresh hematomas)
anti-bacterial action
promotion of wound granulation, with simultaneous reduction of scar tissue.

The invention is based in this connection on, among other things, the discovery that damaged tissue has an increased need for different trace elements and, in this connection, in particular also for zinc and iron. In addition, however, there is also an increased need for other trace elements, particularly metals, in tissue regions of increased activity (defense processes and/or cell proliferation). Since, in accordance with the discovery which forms the basis of the invention, altered tissue, depending on the degree of the damage, increasingly loses the ability, for instance, to reduce zinc this means, in the case of the customary treatment with zinc oxide ointments, that zinc does not pass into solution and therefore also not into action in the corresponding wound, or does so only to a very unsatisfactory extent. In contradistinction to such customary zinc ointments it is, however, possible with the preparation of the invention to feed iron or other trace elements which are essential, i.e. necessary for the body, in acid solution in which these trace elements are completely dissolved and thus can enter fully into action. At the same time, the pH, which is substantially below 7, and preferably less than 4.0, produces a favorable biochemical medium for the activity of endogenous defense.

Although dilute solutions of acids, particularly also of physiological acids, i.e. acids which are endogenous in the human body or related thereto such as, for instance, sulfuric acid, hydrochloric acid, silicic acid, acetic acid and ascorbic acid or citric acid have substantially no pharmacological effect and, in particular, also no detumescent effect aside from a certain anti-bacterial action, and although furthermore metal or metal compounds also have only an extremely limited pharmacological effect, it has been found that the combination of metallic trace elements and acid in aqueous solution which characterizes the invention leads to very surprising, unexpected effects, i.e. due to the synergistic effect of acid and metal the pharmaceutical preparation of the invention in which the essential metallic trace elements are present in ions exerts, even in extremely small concentration, a strongly detumescent, anti-bacterial and wound-healing action. By said synergistic effect, which can be further increased by the use of various physiological acids and/or various essential metallic trace elements, it is possible to prepare very effective pharmaceutical preparations having a low total concentration of the active substances. The preparations prepared in this manner are not only highly effective, but as already mentioned, also very well tolerated.

The form of administration of the preparation of the invention can be optimally adapted to the specific indication or use. Thus it is possible, for instance, to work the preparation of the invention as pharmacologically active component into ointments or creams, or else to apply it directly in liquid form.

In addition to the transdermal use for the treatment of wounds, burns, and other inflammatory changes of the skin and of the subcutaneous cell tissue which has been primarily discussed up to now, the preparation of the invention is suitable, among other things, also for oral administration, in particular in order to eliminate deficiencies of trace elements or to substitute for metallic trace elements in the human or animal body, the above-mentioned synergistic effect between acid and metal and the improved bio-availability obtained thereby leading in this case also to a high rate of absorption.

In practical use it has also been found among other things that upon oral administration of the preparation of the invention for which administration this preparation or solution contains mainly chlorides, the concentration of mineral substances or trace elements in the blood (serum level) frequently increases far more than would be expected on basis of the concentration of the trace elements in the preparation or on basis of the amount of trace elements administered with it. This effect is evidently due to the fact that as a result of the administration of the preparation of the invention, i.e. by the administration of trace elements with excess acid, endogenous blocked trace element depots are activated or opened up. A similar effect can also be noted upon external use of the preparation of the invention.

For the preparation of the invention, the water used can, for instance, be distilled water. Preferably, however, electrolytically demineralized water is used since it has other favorable biological properties. The concentration of the metallic trace elements dissolved as salts or other water-soluble compounds in the water, as well as the ratio of the trace elements to each other, preferably corresponds to the physiological quantity or concentration, i.e. the concentration or quantity in the natural serum or a multiple thereof. The quantity of these metal salts or compounds, which are toxic in large amounts, lies thus within the range of milligrams per liter of solution and, in the same way as the ratio of the metal salts or compounds to each other, is based approximately on the physiological amounts, the latter being possibly also exceeded by a multiple, for instance 2–20 times. Very good results have been obtained, for example, with concentrations of 3 mg of zinc chloride and 6 mg of iron chloride per liter.

An increase in the concentration can in certain cases increase the efficacy of the preparation, the tolerance of the preparation being impaired with increased concentration of metallic trace elements.

As already mentioned above, one essential factor for the efficacy of the preparation of the invention is its pH. Particularly good pharmacological effects have been obtained with pH values within the range of between about 4.0 and 1.0, the pH, to be sure, being preferably less than 3.5. The pH can be adjusted by the addition of a corresponding amount of physiological acid (for instance hydrochloric acid, sulfuric acid, silicic acid, acetic acid, and/or ascorbic acid).

One preparation in accordance with the invention which is suitable, in particular, for the treatment of inflammations by external or internal (oral) use contains, in solution, zinc and iron as metallic trace elements and sulfuric acid as physiological acid in such amount that the solution has a pH within the range of between about 2.0 and 3.0. The proportion of zinc, iron and sulfuric acid is in this connection preferably such that one liter of solution contains about 5 to 30 mg of zinc, about 10 to 50 mg of iron and about 100 to 160 mg of sulfuric acid. Upon use for inflammations, detoxication takes place via sulfates, i.e. the toxic protein compounds present or produced upon inflammations are bound to sulfates and thus neutralized. For external use this preparation forms, for instance, the active principal of an ointment. This preparation can also serve, however, as active principal for a pharmaceutical preparation intended for oral ingestion.

For the production of the preparation of the invention, the most varied methods can, in principle, be used. Thus, for instance, it can be produced in the manner that at least one metal forming an essential metallic trace element, in particular from the group consisting of iron, zinc, manganese, chromium, copper, cobalt, molybdenum, tin, vanadium, nickel and selenium, is brought, preferably in comminuted or powdered form, with acid and water into solution, the pH of the solution then being adjusted, for instance, by the amount of water added and/or by the amount of acid added.

Furthermore it is also possible to produce the preparation of the invention in the manner that at least one water-soluble metal compound of an essential metallic trace element, for instance zinc chloride, iron chloride or chromium oxide, is dissolved in water with the addition of the physiological acid, the necessary pH being established in this case also by the amount of water and/or of acid added.

The preparation of the invention contains, in addition to the essential metallic trace elements, preferably also essential nonmetallic trace elements, selected, for instance, from the group consisting of silicon, iodine and fluorine, which are also contained in the preparation in a physiological quantity or a multiple thereof.

A preferred method of preparing the preparation of the invention will be explained in further detail below with reference to the drawing, which shows in a simplified cross section an arrangement for the production of the preparation by electrolysis.

In the drawing, FIG. 1 is a container of electrically non-conductive material, for instance glass or plastic. A substantially neutral aqueous starting solution which contains chlorides and/or sulfates dissolved in water is introduced into the container 1. Two electrodes 3 and 4 extend into this starting solution 2 in such a manner that these electrodes 3 and 4 are arranged at a predetermined distance from each other within the container. The two electrodes 3 and 4 are so connected to a source of direct voltage, not shown in detail, that the electrode 3 acts as cathode and the electrode 4 as anode. Between the two electrodes there are arranged two membranes or diaphragms 5 and 6 so that the inside of the container 1 is divided substantially into three zones by these membranes 5 and 6, namely into the zone 7 lying in the region of the electrode 3 or cathode, the zone 8 lying in the region of the electrode 4 or anode, and the zone 9 lying between the zones 8 and 7. The membranes 5 and 6 are made of a suitable material, for instance clay, fabric or felted material, and have such a density that ionization of the starting solution 2 is possible by the electrodes 3 and 4 which are connected to the source of direct voltage; however, at the same time, the membranes 5 and 6 assure a concentrating of the acid portion ($H^+$) obtained upon the ionization of the electrolysis in the region of the zone 7 and a concentrating of the basic portion ($OH^-$) obtained upon the electrolysis in the region of the zone 8, and the separation of the two zones 7 and 8 by the central zone 9 prevents possible precipitation. With such an arrangement, which permits of a reproducible manner of operation, the electrode 3 which forms the cathode consists of at least one metal suitable for the formation of an essential metallic trace element or an alloy of such metals. Upon the electrolysis, the at least one metal forming the electrode 3 or the metal alloy forming the electrode 3 is dissolved in the zone 7 so that an acid solution of increasing concentration of essential metallic trace elements is obtained there. Of course it is possible also to provide several electrodes 3 of different or the same metals and/or of different or the same alloys in the zone 7. It is also possible to use 10 more than one electrode 4 in the zone 8. Furthermore, it is also possible to provide, in addition to the electrode 3 within the zone 7, another, neutral electrode which, in contradistinction to the electrode 3 or several such electrodes 3, does not pass into solution.

In order to be able to adjust the desired concentration of metallic trace element or elements in the zone 7, at least the electrode or electrodes 3 present there are held in an adjustable mount which permits a decrease or increase of the depth of immersion of the electrodes, as required.

Instead of the membranes 5 and 6, at least one membrane developed as a tube can also be used, preferably such a membrane which is made of water-pervious fired clay. The electrodes used are then so arranged within said at least one membrane that, depending on the arrangement, either the acid or the alkaline portion is concentrated by the electrolysis within the corresponding tubular membrane.

The pharmaceutical preparation of the invention may also be to treat animals including humans, suffering from a virus, comprising administering to the sufferer an anti-viral effective amount of the preparation to obtain an anti-viral effect. The pharmaceutical preparation of the invention may further be used as a suntan composition, such as a suntan lotion, cream and the like, since the metal trace elements promote the formation of melanin in the human body upon exposure of the human body to UV radiation after topical application to the skin of the pharmaceutical composition of the invention in an amount effective to promote tanning of the skin.

I claim:

1. A pharmaceutical preparation suitable for oral or transdermal administration for the treatment of wounds, damaged tissue, and inflammation in animals, including humans, which comprises a solution of water and at least one essential metallic trace element or salt thereof selected from the group consisting of iron, zinc, manganese, chromium, copper, cobalt, molybdenum, tin, vanadium, nickel and selenium and salts thereof, said metallic trace metal or salt thereof being contained in the solution in a physiological quantity, the pH of the solution being less than 4.

2. A pharmaceutical preparation according to claim 1, wherein the pH of the solution is adjusted by the addition of at least one physiological acid selected from the group consisting of hydrochloric acid, sulfuric acid, silicic acid, ascorbic acid, and acetic acid.

3. A pharmaceutical preparation according to claim 1, wherein the pH of the solution is within the range of between about 4.0 and 1.0.

4. A pharmaceutical preparation according to claim 1, wherein the pH of the solution is less than 3.5.

5. A pharmaceutical preparation according to claim 4, wherein the pH of the solution is between about 2.0 and 3.0.

6. A pharmaceutical preparation according to claim 5, wherein the solution comprises zinc and iron and a physiological acid in such a quantity that the pH of the solution is between about 2.0 and 3.0.

7. A method for the treatment of wounds, damaged tissue, and inflammation in animals, including humans, which comprises administering to a human or animal in need thereof a therapeutically effective amount of the pharmaceutical preparation of claim 1.

8. A pharmaceutical preparation suitable for oral or transdermal administration for the treatment of wounds, damaged tissue and inflammation in animals, including humans, which comprises an aqueous solution comprising water and about 5 to 30 mg per liter of zinc, about 10 to 50 mg per liter of iron and 100 to 150 mg per liter of sulfuric acid, said solution having a pH between about 2.0 and 3.0.

* * * * *

UNITED STATES PATENT AND TRADEMARK OFFICE
CERTIFICATE OF CORRECTION

PATENT NO. : 5,079,010
DATED : January 7, 1992
INVENTOR(S) : Siegfried Natterer

It is certified that error appears in the above-identified patent and that said Letters Patent is hereby corrected as shown below:

Title page:

In item [76] the first name of the inventor should read --Siegfried--.

Signed and Sealed this

Fourth Day of May, 1993

Attest:

MICHAEL K. KIRK

*Attesting Officer*     *Acting Commissioner of Patents and Trademarks*